(12) United States Patent
Grimes et al.

(10) Patent No.: US 7,482,314 B2
(45) Date of Patent: Jan. 27, 2009

(54) MICRODERMABRASION COMPOSITION AND KIT

(75) Inventors: Pearl E. Grimes, Los Angeles, CA (US); Irwin Palefsky, Clifton, NJ (US); Ken Klein, Fairlawn, NJ (US); Ni'kita Wilson, Union, NJ (US)

(73) Assignee: Orchid Scientific, Inc., Beverly Hills, CA (US)

( * ) Notice: Subject to any disclaimer, the term of this patent is extended or adjusted under 35 U.S.C. 154(b) by 446 days.

(21) Appl. No.: 10/195,008

(22) Filed: Jul. 11, 2002

(65) Prior Publication Data

US 2004/0010269 A1 Jan. 15, 2004

(51) Int. Cl.
*A61K 7/00* (2006.01)

(52) U.S. Cl. .................. 510/130; 510/136; 510/139; 424/401; 606/131

(58) Field of Classification Search ............ 510/130, 510/139; 424/70.1, 401
See application file for complete search history.

(56) References Cited

U.S. PATENT DOCUMENTS

| | | | |
|---|---|---|---|
| 2,958,593 A | 11/1960 | Hoover et al. | |
| 3,574,854 A | 4/1971 | Bossard | |
| 3,867,522 A | 2/1975 | Kligman | |
| 4,188,447 A | 2/1980 | Ehlenz | |
| 4,203,857 A | 5/1980 | Dugan | |
| 4,459,987 A | 7/1984 | Pangburn | |
| 4,572,187 A | 2/1986 | Schetrumpf | |
| 5,116,606 A | 5/1992 | Alt | |
| 5,753,245 A | 5/1998 | Fowler et al. | |
| 5,800,446 A | 9/1998 | Banuchi | |
| 5,811,111 A | 9/1998 | McAtee et al. | |
| 5,954,730 A | 9/1999 | Bernabei | |
| 5,971,999 A | 10/1999 | Naldoni | |
| 6,017,351 A | 1/2000 | Street | |
| 6,017,561 A | 1/2000 | Zhou et al. | |
| 6,241,739 B1 | 6/2001 | Waldron | |
| 6,283,978 B1 | 9/2001 | Cheski et al. | |
| 6,306,147 B1 | 10/2001 | Bernabei et al. | |
| 6,309,655 B1 * | 10/2001 | Minnix | 424/401 |
| 6,322,568 B1 | 11/2001 | Bernabei et al. | |
| 6,375,964 B1 | 4/2002 | Cornelius | |
| 6,432,114 B1 | 8/2002 | Rosso | |
| 6,440,433 B1 * | 8/2002 | Breton et al. | 424/401 |
| 2001/0009674 A1 | 7/2001 | Deckner et al. | |
| 2001/0018061 A1 | 8/2001 | Rhoades | |
| 2001/0046506 A1 | 11/2001 | Rhoades | |
| 2002/0086039 A1 * | 7/2002 | Lee et al. | 424/401 |
| 2002/0087167 A1 | 7/2002 | Winitsky | |

(Continued)

OTHER PUBLICATIONS

Tsai et al., *Aluminum Oxide Crystal Microdermabrasion*, Dermatol Surg 1995, vol. 21, pp. 539-542, nma.

(Continued)

*Primary Examiner*—Necholus Ogden, Jr.
(74) *Attorney, Agent, or Firm*—Pearne & Gordon LLP

(57) ABSTRACT

A microdermabrasion composition is provided. The composition preferably has 2-60 weight percent surfactant, 5-60 weight percent volatile silicone oil, 8-50 weight percent anhydrous solvent, and 1-25 weight percent water soluble salt. The water soluble salt is most preferably sodium chloride. The composition is effective and safe for in-home microdermabrasion. A kit including such a microdermabrasion composition and an applicator sponge, and a method of microdermabrasion are also provided.

46 Claims, 1 Drawing Sheet

U.S. PATENT DOCUMENTS

| | | |
|---|---|---|
| 2002/0090385 A1 | 7/2002 | Fox et al. |
| 2002/0098210 A1 | 7/2002 | Hahn et al. |
| 2003/0049291 A1 | 3/2003 | Cheski |
| 2003/0049995 A1 | 3/2003 | Schutz et al. |
| 2003/0133900 A1* | 7/2003 | McLaughlin .............. 424/70.22 |
| 2003/0211062 A1* | 11/2003 | Laden et al. ................ 424/70.1 |

OTHER PUBLICATIONS

Yosipovitch et al., *Time-Dependent Variations of the Skin Barrier Function in Humans: Transepidermal Water Loss, Stratum Corneum Hydration, Skin Surface pH, and Skin Temperature*, The Journal of Investigative Dermatology, vol. 110, No. 1, Jan. 1998, pp. 20-23.

B. Eberlein-König et al., *Skin Surface pH, Stratum Corneum Hydration, Trans-Epidermal Water Loss and Skin Roughness Related to Atopic Eczema and Skin Dryness in a Population of Primary School Children*, Acta Derm Venereol 2000, vol. 80, pp. 188-191, nma.

Shim, et al., *Microdermabrasion: A Clinical and Histopathologic Study*, Dermatol Surg vol. 27, No. 6, Jun. 2001, pp. 524-530.

Hernandez-Perez et al., *Gross and Microscopic Findings in Patients Undergoing Microdermabrasion for Facial Rejuvenation*, Dermatol Surg vol. 27, No. 7, Jul. 2001, pp. 637-640.

* cited by examiner ly exfoliation has become a mainstay of in-home cleansing routines. Exfoliation procedures and products facilitate maintenance of the health and beauty of skin, in particular facial skin. Such products are also used by many people as part of an anti-aging regimen. Microdermabrasion is one technique of superficial exfoliation that has enjoyed immense popularity in recent years. Microdermabrasion as a cosmetic procedure to improve the suppleness and appearance of facial skin has been widely practiced by dermatologists and other skin care professionals for over a decade. Recently, the use of microdermabrasion to treat skin conditions or defects such as acne, scarring, and the like has gained significantly in popularity.

MICRODERMABRASION COMPOSITION AND KIT

BACKGROUND OF THE INVENTION

1. Field of the Invention

The invention relates to a composition for performing microdermabrasion on skin. More particularly, it relates to a composition suitable for microdermabrasion by an individual in his or her home.

2. Description of Related Art

Superficial exfoliation has become a mainstay of in-home cleansing routines. Exfoliation procedures and products facilitate maintenance of the health and beauty of skin, in particular facial skin. Such products are also used by many people as part of an anti-aging regimen. Microdermabrasion is one technique of superficial exfoliation that has enjoyed immense popularity in recent years. Microdermabrasion as a cosmetic procedure to improve the suppleness and appearance of facial skin has been widely practiced by dermatologists and other skin care professionals for over a decade. Recently, the use of microdermabrasion to treat skin conditions or defects such as acne, scarring, and the like has gained significantly in popularity.

The technology of microdermabrasion was developed in Europe and subsequently marketed in the United States. Most microdermabrasion units are closed loop negative pressure systems which pass aluminum oxide crystals onto the skin while simultaneously vacuuming used crystals away. Other systems utilize sodium chloride and positive pressure for superficial skin resurfacing. These systems are expensive and not appropriate for safe use in the home by an untrained individual.

Though reserved for use by a trained professional, the effectiveness of conventional microdermabrasion systems as described above and associated techniques of microdermabrasion have been demonstrated in the literature; see, e.g., Ren-Yeu Tsai, Chen-Nai Wang, Heng-Leong Chan, *Aluminum Oxide Crystal Microdermabrasion*, Dermatol. Surg., vol. 21, pp. 539-542, 1995, and Elisabeth K. Shim, David Barnette, Kathi Hughes, Hubert T. Greenway, *Microdermabrasion: A Clinical and Histopathologic Study*, Dermatol. Surg., vol. 27, pp. 524-530, 2001.

A key limitation to these conventional microdermabrasion systems and techniques is that they are performed by a dermatologist or other qualified skin care professional. It would be desirable to provide a microdermabrasion system that is suitable for home use, and that is within the scope of what an average person could perform at home as part of his or her hygienic regimen. Preferably, such a system would include a composition suitable for in-home application, and would not involve specialized machinery that would require specialized expertise or be cost-prohibitive. Preferably, the composition would not impair or reduce the barrier function of the skin, and most preferably would improve skin barrier function following microdermabrasion.

SUMMARY OF THE INVENTION

A microdermabrasion composition is provided that has at least one water soluble abrasive component in an anhydrous fluid medium.

A kit for microdermabrasion is also provided. The kit includes a microdermabrasion composition and an applicator sponge. The composition has 1-25 weight percent water soluble salt in an anhydrous fluid medium. The applicator sponge is made from polymeric foam.

A method of performing microdermabrasion is provided that includes the following steps: a) providing a microdermabrasion composition that has at least one water soluble abrasive component in an anhydrous fluid medium; b) identifying a target area of one's skin for microdermabrasion treatment; c) applying a quantity of the composition to the identified target area of skin; and d) massaging the composition into the target area.

DETAILED DESCRIPTION OF THE PREFERRED EMBODIMENTS OF THE INVENTION

Figure 1:
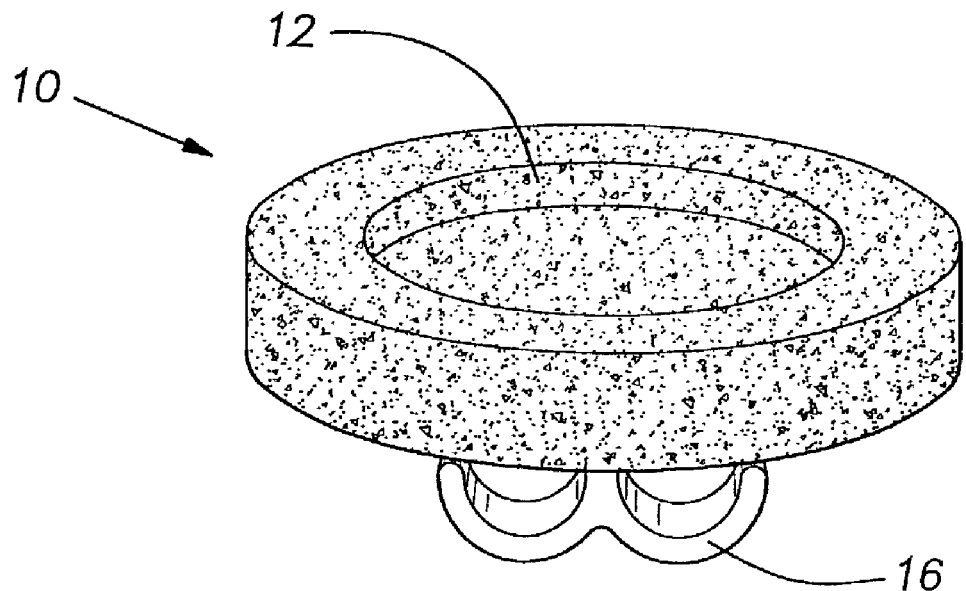
FIG. 1 is a diagrammatic view of a preferred microdermabrasion applicator sponge with a first handle according to the invention.

As used herein, when a range is given such as 5 to 25 (or 5-25), this means preferably at least 5 and, separately and independently, preferably not more than 25. Unless otherwise explicitly indicated, all concentrations expressed herein are percentages by weight. As used herein and in the claims, the term fluid medium includes creams, pastes, gels, lotions, and other flowable fluid or liquid media. The term fluid medium shall not include gases.

Provided is a microdermabrasion composition for in-home microdermabrasion. The composition is dispensed preferably from a soft tube, less preferably from a jar, bottle, pump, can, spray can or spray bottle, less preferably from some other known container. The composition comprises at least one water soluble abrasive component in an anhydrous fluid medium or system. Preferably, the fluid medium is a flowable fluid medium. The composition preferably includes the components listed in table 1 below. In table 1, any preferred or less preferred or more preferred concentration or range of any component can be combined with any preferred or less preferred or more preferred concentration or range of any of the other components; it is not required or necessary that all or any of the concentrations or ranges come from the same column. The column labeled "Phase" refers to the preferred order and method of mixing the components, and is explained in detail below. The column labeled "Trade Name" refers to the trade name or trademark of a preferred commercially available formulation of the associated preferred ingredient. However, other commercially available suitable formulations of each preferred ingredient can be used. All values in table 1 are percentages by weight.

TABLE 1

Preferred composition of microdermabrasion preparation for home use

| Phase | Component | Preferred Ingredient | Trade Name | Preferred | Less Preferred | Less Preferred |
|---|---|---|---|---|---|---|
| A | Surfactant | Sodium Lauryl Sulfoacetate | Lanthanol LAL | 15<br>10-16 | 8 20<br>5-30 | 6-40<br>4-50<br>2-60 |
| A | Surfactant | Cetearyl Alcohol and Ceteareth-20 | Lipowax D | 4<br>3.5-6 | 3-10<br>2-15 | 1-20<br>1-30<br>0-40 |
| A | Volatile silicone oil | Dimethylcyclosiloxane | DC-345 fluid | 20<br>22-28 | 15-30<br>10-35 | 10-40<br>8-50<br>5-60 |
| A | Emollient ester/ solvent | Caprylic/Capric triglyceride | Liponate GC | 9<br>8.5-9.5 | 8-10<br>6-12 | 5-15<br>4-20<br>0-25 |
| A | Thickener | Castor Oil, hydrogenated castor oil based additive | Thixcin R/ Rheocin | 0.25<br>0.24-0.26 | 0.22-0.28<br>0.2-0.3 | 0.15-0.35<br>0.1-0.4<br>0-0.5 |
| A | Anhydrous Solvent | Paraffinic, preferably isoparaffinic hydrocarbon | Isopar L | 21<br>19-22 | 18-23<br>15-25 | 12-30<br>10-40<br>8-50 |
| A | Vitamin E | Vitamin E Acetate | — | 0.2<br>0.10-0.21 | 0.08-0.22<br>0 05-0.25 | 0.1-0.3<br>0.05-0.35<br>0-0.4 |
| B | Water soluble emollient | Butylene glycol | — | 3<br>2.9-3.2 | 2.8-3.5<br>2.5-3.8 | 2-4<br>1-4.5<br>0-5 |
| B | Water soluble emollient | Silicone glycol copolymer | DC-193 fluid | 6.00<br>5.5-6.8 | 5-7<br>4-8 | 3-9<br>1.5-10<br>0-15 |
| B | Antimicrobial | Propylene Glycol/Urea/ Propyl Paraben | Germaben II | 1<br>0.9-1.1 | 0.8-1.2<br>0.6-1.4 | 0.4-1.6<br>0.2-1.8<br>0-2 |
| B | Fragrance | — | Intrarome BQT#40080 | 0.3<br>0.28-0.35 | 0.25-0.4<br>0.2-0.5 | 0.1-0.8<br>0.05-1<br>0-5 |
| B | Abrasive | Sodium chloride crystals | — | 8<br>7.5-8.5 | 7-9<br>6-10<br>5-11 | 4-12<br>3-13<br>2-14<br>1-15 |
| B | Abrasive | Sodium bicarbonate | — | 7<br>6.5-7.5 | 6-8<br>5-9 | 4-10<br>3-11<br>2-15 |

It will be understood by persons of ordinary skill in the art that additional components, not listed in table 1, which are known or conventional in the art can be added to the invented composition in conventional amounts to impart desirable properties thereto; i.e. colorants, emulsifiers, etc.

In table 1, all components except the abrasive components form a part of the anhydrous fluid medium. In the composition, the water soluble abrasive material is mixed or dispersed in the anhydrous fluid medium. The composition is applied to a target skin area for microdermabrasion treatment (described below). Following a treatment, the composition is rinsed away from the skin with ordinary tap water. The composition preferably contains components to aid or promote dispersion of the composition in water (described below) to facilitate rinsing of the skin free of the composition. Also, the abrasive components, themselves being water soluble, are dissolved and rinsed away so as to prevent leaving any abrasive particulate or particulate residue on the treated skin following microdermabrasion.

The abrasive component preferably comprises a water soluble abrasive material, preferably a water soluble salt, most preferably sodium chloride crystals as indicated in table 1. Less preferably, other suitable water soluble salts can be used, e.g. potassium chloride, magnesium chloride, aluminum hydroxide, etc. Preferably, the water soluble salt has a mean particle size distribution of 50-2000, preferably 75-1500, preferably 100-1000, preferably 125-900, preferably 150-850, microns. In the preferred composition, a second abrasive component is added having a finer mean particle size distribution relative to the sodium chloride crystals described above. Most preferably, this second abrasive component is sodium bicarbonate powder having a mean particle size distribution of 20-500, preferably 50-400, preferably 75-350, preferably 100-300, microns. Less preferably, other water soluble abrasive powders conventional in the art can be used as the second abrasive component so long as they have a similar mean particle size distribution as stated above. Sodium bicarbonate is preferred because it is an effective abrasive or skin-abrading material that does not impart the harsh, scratchy feel of sodium chloride and other inorganic salt crystals, e.g. aluminum oxide. Also, the sodium bicarbonate abrasive component significantly reduces the potential for an unskilled or untrained person to cause severe skin damage through misuse of the microdermabrasion composition in the home. The combination of sodium chloride crystals and sodium bicarbonate powder as above described and listed in table 1 is most preferred because this combination provides an effective skin-abrading system for in-home microdermabrasion while minimizing abrasive irritation and harshness likely to cause skin damage from over- or improper use. Thus, the described combination of sodium chloride crystals and sodium bicarbonate powder is well suited for in-home microdermabrasion.

The surfactant components preferably serve the following functions: to provide mild detergency for cleansing the skin prior to, during and immediately following microdermabrasion; and to aid or promote dispersion of the composition in water. It has been discovered that the combination of Lanthanol LAL and Lipowax D in the above-stated weight percentage proportions (table 1) effectively serves these functions. Specifically, Lanthanol LAL (sodium lauryl sulfoacetate) is a mild detergent for cleansing the skin, and Lipowax D (commercially available mixture of cetearyl alcohol and ceteareth-20) is an effective emulsifier to help emulsify the microdermabrasion composition in water. This aids in rinsing the composition from the skin with water following a microdermabrasion treatment. (Lipowax D is a trademark of Lipo Chemicals, Inc., Paterson, N.J.). Less preferably, other suitable surfactants or surfactant combinations can be used.

The composition preferably comprises a combination of silicone oil and an emollient ester. The silicone oil is preferably DC-345 fluid (from Dow Corning) which is a volatile silicone oil that volatilizes at approximately the same rate as water. The silicone oil aids solubilization and emulsification of the organic components of the microdermabrasion composition, as well as provides a smooth texture to the composition. The preferred emollient ester, Liponate GC, is a medium-chain triglyceride (caprylic/capric triglyceride) derived from coconut oil. The emollient ester counters the drying effect of the organic solvent component (described below). The emollient ester also acts as a makeup remover solvent and effectively counters the drying out that can be caused by organic solvents. This is, in part it is believed, because the preferred or suitable emollient esters have a structure similar to natural skin oil. Therefore, the emollient ester replenishes the natural skin oil that is removed or solvated by the organic solvent in the composition.

The thickener component prevents or substantially prevents or minimizes oil or other organic components from bleeding out of (or phase separating from) the invented composition. In addition, the thickener increases the viscosity of the composition to provide a creamy consistency. Preferred thickeners are Thixcin R and Rheocin. Thixcin is available from Rheox, Inc., Hightstown, N.J., and Rheocin is available from Süd-Chemie Rheologies, Louisville, Ky.

The solvent is an organic solvent, preferably a paraffinic solvent, preferably an isoparaffinic solvent, preferably Isopar L from Exxon-Mobil Corporation, Houston, Tex. Isopar L is a known synthetic isoparaffinic hydrocarbon solvent that is substantially nontoxic and has a high molecular weight. Less preferably, other suitable high molecular weight non-toxic organic solvents, preferably paraffinic or isoparaffinic solvents, can be used. Organic solvents, such as Isopar L, are effective solvents for makeup ingredients but can also solvate natural skin oil thereby drying out human skin. In the invented composition, this drying out effect is preferably countered by an emollient ester component as described above.

The composition preferably contains vitamin E, preferably vitamin E acetate to prevent discoloration and odor generation. Vitamin E acetate is a conventional anti-oxidant and is effective to prevent rotting and rancidity of the invented composition after repeated use.

The composition also preferably contains a water-soluble emollient component or mixture of components effective to enhance or provide moisturization properties to the invented composition upon contact with water. The water-soluble emollient prevents or substantially prevents drying out of the skin once the microdermabrasion composition is washed from the skin (i.e. the face) of the person using it. Once a person has performed microdermabrasion on his skin (described below), the composition is washed away with water. The water-soluble emollient components prevent drying out the skin from the cleansing and/or solvent action of the other composition components by imparting moisturizing properties to the composition upon contact with the rinsing water. In this manner, skin is moisturized as the composition is cleansed away following in-home microdermabrasion. The preferred water-soluble emollients are listed above in table 1, (butylene glycol and DC-193 fluid from Dow Corning). Less preferably, other suitable water-soluble emollients conventional in the art can be used.

Preferably, the invented microdermabrasion composition also contains an antimicrobial agent such as Germaben or Germaben II from ISP, Inc. The antimicrobial agent is a preservative to kill bacteria and fungus introduced into the product during consumer use.

The invented composition preferably has a viscosity of 500,000-4,000,000 centipoise at 25° C., preferably 600,000-2,000,000, preferably 800,000-1,500,000, preferably 900,000-1,300,000, preferably 900,000-1,100,000, preferably about 1,000,000, centipoise at 25° C., providing a creamy microdermabrasion composition in the form of a paste.

A preferred microdermabrasion composition according to the invention is prepared as follows. All of the phase A components from table 1 are mixed together and heated to about 60° C. The mixture is continuously stirred until the composition is uniform at this temperature. Once uniform, the mixture is cooled slowly, preferably at a rate of about 0.5-10, preferably 0.8-8, preferably about 1-5, degrees Celsius per minute, to a temperature of about 45° C. The components of phase B are separately mixed together at room temperature, more preferably at about 45° C., and the phase B mixture is added to the phase A mixture at 45° C. to form a combined mixture of the phase A and phase B components. The combined mixture is mixed until uniform, and then cooled with mixing to room temperature, e.g. 25° C., to provide a preferred microdermabrasion composition. The above-disclosed method is a preferred method of making the invented composition from its components. However, other methods will be apparent to those skilled in the art which will not significantly or substantially detract from the efficacy of the invented composition.

The invented microdermabrasion composition is effective to achieve improved skin appearance and suppleness, as well as to reduce or minimize the appearance of scarring, particularly facial scarring, from acne, surgery, trauma, etc., as well as stretch marks and other skin defects. In one embodiment, the invented microdermabrasion composition is preferably used by a person in the home as follows. First, the person identifies a target area of his or her skin for microdermabrasion treatment. He then applies a quantity of the invented composition to the surface of an applicator, preferably a sponge, to provide an even layer of the composition on the application surface. For in-home microdermabrasion of the face, the application surface (the surface of the applicator to which the composition is applied) preferably has dimensions about 3 cm×3 cm, less preferably any other suitable dimensions. The application surface is then applied to the target skin surface and the skin is massaged by a rotary motion (i.e. in a circular pattern) taking care to avoid contact with one's eyes for 1-8, preferably 2-6, preferably 3-4, revolutions or passes per surface area of the skin to be treated. Once microdermabrasion is complete, the composition is washed away from the treated skin with ordinary tap water. Moisturizers are then preferably applied for the next 24 to 48 hours. Preferably, microdermabrasion can be performed as described above bi-weekly or monthly, less preferably some other interval, though preferably not more often than bi-weekly.

In another, more preferred embodiment, the applicator sponge is a circular applicator sponge 10 having a recess portion 12 for retaining the invented composition as shown in FIG. 1 and described in detail below. The method of use (performing microdermabrasion) using this preferred applicator sponge 10 is substantially similar to that described in the preceding paragraph, except that in this embodiment the composition is provided within the recess portion 12 of the sponge 10, and not on an application surface as described above. Other aspects of the preferred applicator sponge 10 are described more fully below.

This technique of in-home microdermabrasion provides improved skin texture and overall facial appearance comparable to salon or physician in-office microdermabrasion treatments. Use of the invented composition for in-home microdermabrasion does not harm or substantially impair skin barrier function over an extended period. Preferably, the skin's barrier function (stratum corneum integrity) returns to (or is improved from) its pre-treatment state within 96, preferably 72, preferably 48, preferably 24, hours following in-home microdermabrasion using the invented composition.

The preferred composition from table 1 is designed for in-home use and requires no special skill or training. It is an effective microdermabrasion composition that is gentle enough to prevent serious harm or injury to the skin from occasional or moderate unskilled misuse.

The invented composition can be modified according to a second preferred embodiment of the invention to provide a higher strength microdermabrasion composition suitable for professional use. Such a professional strength composition is provided by increasing the concentration of sodium chloride crystals in the composition, and preferably has sodium chloride crystals in a concentration of 8-25, preferably 9-20, preferably 10-18, preferably 11-15, preferably about 12, weight percent. In this embodiment, the concentration of the surfactant component or components (preferably Lanthanol LAL) from table 1 is reduced to accommodate the additional sodium chloride crystals, with all other components having substantially the same preferred weight percent concentrations as listed in table 1. Alternatively, the concentration of sodium chloride crystals in the composition can be 1-25 weight percent.

Figure 2:
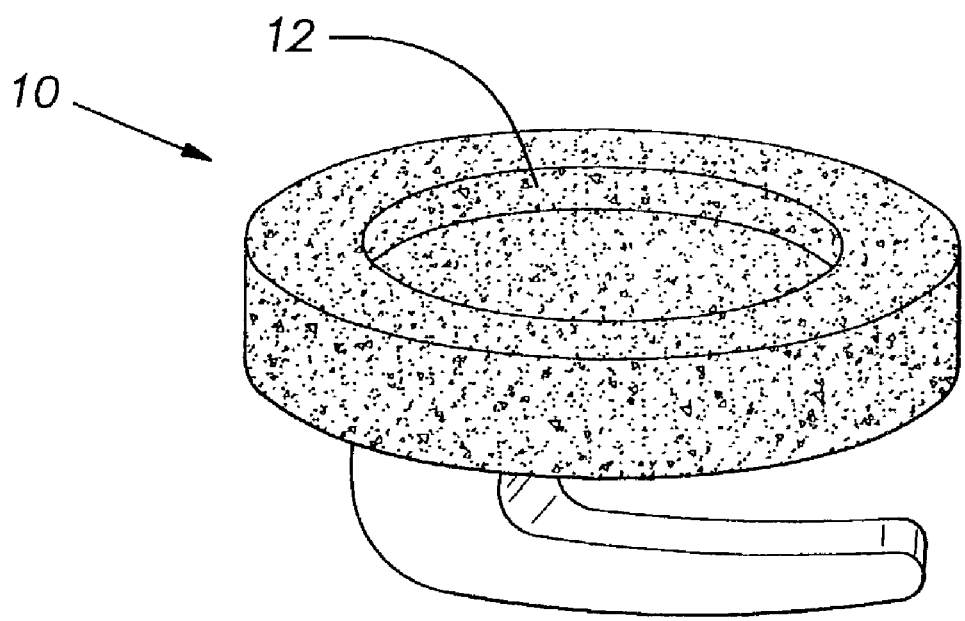
FIG. 2 is a diagrammatic view of the applicator sponge of FIG. 1, but with a second preferred handle.

Most preferably, (whether in-home strength or professional strength) the invented composition is applied with an applicator sponge 10 according to the invention as shown in FIGS. 1 and 2. The applicator sponge 10 is preferably a cosmetic sponge as known in the art, preferably circular, less preferably, any other suitable shape, e.g. square, triangular, oval, etc., that has been modified as follows. The sponge 10 has a recess portion 12 arranged concentrically therein as shown in the figures, which is open to one face of the sponge 10 but does not penetrate through to the opposite face of the sponge. The recess portion 12 is adapted to retain the invented microdermabrasion composition therein and against the skin surface during a microdermabrasion treatment. In practice, a quantity of the invented composition is applied to the recess portion 12 in sponge 10, and then massaged against the target skin area in a circular pattern as described above. Optionally and preferably, the sponge 10 is attached or adhered to a handle 16 as shown in the figures for ease of use, and so that the sponge 10 does not slip out of one's hand while rubbing in the preferred circular pattern during microdermabrasion as described above. Sponge 10 is preferably adhered to the handle 16 via an adhesive, less preferably adhesive tape, less preferably another suitable and conventional adhesive. FIG. 1 shows a sponge adhered to a first preferred handle, and FIG. 2 shows a sponge adhered to a second preferred handle. Less preferably, other handle configurations can be used.

The sponge 10 is preferably a closed cell polymeric foam sponge, made from a closed cell polymeric foam. By closed cell, it is meant that the foam cells within the sponge 10 are nonporous or substantially nonporous such that there is no (or substantially no) bulk or superficial fluid communication between adjacent foam cells. (Bulk or superficial fluid communication refers to the bulk flow of a fluid phase, and not necessarily other transport mechanisms such as diffusion). Preferably, the foam is a rigid foam, semi-rigid foam, or flexible foam conventional in the art, most preferably a flexible foam, most preferably flexible polyurethane foam. The sponge 10 is preferably made from the preferred material via known or conventional methods. The sponge 10 has an outer diameter of preferably about 6, less preferably 5-7, less preferably 3-8, centimeters, with the recess portion 12 having a diameter of preferably about 4.5, less preferably 4-5, less preferably 3-5, less preferably 1-6, centimeters, and a depth of about 0.3-0.5, less preferably 0.2-0.6, less preferably 0.1-0.7, less preferably 0.1-1, centimeters. Preferably, the sponge 10 has a depth (height) at least or about twice the depth of the recess portion 12 in order to provide sufficient rigidity to the sponge 10 to keep its shape during microdermabrasion as the sponge 10 is rubbed against the target skin surface area, preferably in a circular pattern as described above. For example, a sponge having a recess portion 12 of 0.5 centimeters depth, preferably has an overall depth (height) of about or at least 1 centimeter.

Without wishing to be bound by a particular theory, it is believed that an applicator sponge 10 having a recess portion 12, and made from a closed cell polymeric foam as described, aids effective microdermabrasion as follows. The sponge 10 with recess portion 12 promotes maximum contact of the sodium chloride crystals with the skin area being treated. The recess portion 12 has sufficient diameter and recess volume to allow adjacent crystals to abrade the skin surface as the skin is massaged in the preferred circular pattern without the crystals substantially grinding together and disintegrating. This reduces abrasive crystal loss through attrition. In addition, it is believed that the closed cell foam of the sponge 10 prevents or substantially prevents the microdermabrasion composition from absorbing or diffusing into the sponge from within the recess volume, away from the skin surface during treatment. This helps keep the composition against the skin during microdermabrasion. A closed cell foam applicator sponge 10 having recess portion 12 effectively retains the sodium chloride crystals within the recess portion 12 and against the target skin area as the sponge 10 is massaged over the skin surface in the preferred circular pattern.

In a less preferred embodiment, the composition can be applied using a cotton sponge or other suitable applicator conventional in the art.

Most preferably, the invented composition contains at least one functional additive listed in table 2 below. In table 2, any preferred or less preferred or more preferred concentration or range of any component can be combined with any preferred or less preferred or more preferred concentration or range of any of the other components; it is not required or necessary that all or any of the concentrations or ranges come from the same column. The columns labeled "Phase" and "Trade Name" are the same as for table 1 above. All values in table 2 are percentages by weight in the invented composition.

TABLE 2

Functional additives for invented composition

| Phase | Component | Preferred Ingredient | Trade Name | Preferred | Less Preferred | Less Preferred |
|---|---|---|---|---|---|---|
| B | Keratolytic agent | Salicylic acid | — | 0.5-2 | 0.2-3<br>0.3-2.5 | 0.1-5<br>0.15-4<br>0-4 |
| B | Oxidizer | Benzoyl peroxide | — | 5-10 | 2-15<br>3-12 | 1-20<br>1.5-18<br>0-18 |
| B | Antibacterial | Triclosan | Irgasan dp-300 | 0.1-0.3 | 0.05-0.70<br>0.08-0.5 | 0.02-1.5<br>0.04-1<br>0-1 |
| B | Skin smoothing agent | Vitamin A Alcohol | Retinol | 0.01-0.3 | 0.005-0.4<br>0.005-0.5 | 0.005-0.6<br>0.001-0.7<br>0-1 |

The keratolytic agent is effective to remove dead keratin cells (skin cells) from the surface of the skin being treated via home-microdermabrasion. The preferred keratolytic agent is salicylic acid, though other conventional keratolytic agents (including glycolic acid and lactic acid) can be used in conventional amounts. The oxidizer is a cleansing component to cleanse the skin following and during microdermabrasion. The oxidizer is also effective to remove adherent dead skin or keratin cells from the skin surface being treated. The preferred oxidizer is benzoyl peroxide, though other oxidizers can be used in conventional amounts. An antibacterial component can also be added to remove nascent or other unwanted bacteria from the skin surface being treated. This can be especially important because skin barrier function can be temporarily reduced or impaired immediately following microdermabrasion. Hence, it is desirable to remove any bacteria that might otherwise penetrate the skin following microdermabrasion. The preferred antibacterial component is triclosan, preferably available under the trade name Irgasan dp-300. It is also preferred to add a skin smoothing agent to the invented composition, preferably retinol, which is a vitamin-A alcohol. Retinol is a skin improving agent effective to smooth treated skin following microdermabrasion using the invented composition. Retinol also has keratolytic properties.

The functional additives listed in table 2 are skin beneficial ingredients and are optionally and preferably included in the invented composition in the stated quantities. The functional additives from table 2 are water activated; that is, their above described functions are activated or enhanced upon contact with water. Thus, the invented composition containing one or more of the functional additives listed in table 2 is preferably used as follows.

First, a microdermabrasion treatment is carried out as described in detail above. However, following microdermabrasion, the composition is not immediately rinsed from the treated skin area. Instead, moisture is added to the composition while it is still present on the treated skin area to impart water to and activate the functional additives. To add moisture to the composition on the skin, a damp cloth or sponge can be used, optionally with gentle rubbing (i.e. in a circular motion) against the skin to disperse the water throughout the composition. Alternatively, water can be poured onto the composition on the skin surface following microdermabrasion treatment. Once wetted, the composition is left on the treated skin area for a period of time, preferably less than 5 minutes, preferably 10 seconds to 4 minutes, preferably 15 seconds to 3 minutes, preferably 20 seconds to 2 minutes, preferably 30 seconds to 1 minute, to afford the functional additives time to work. Subsequently, the wetted composition is rinsed away from the treated skin area in a known or conventional manner. Hence, the invented composition containing one or more of the above functional additives is used as part of a two-step skin improvement process; first the skin is microdermabraded to exfoliate dead, outer skin layers, and second the newly exposed underlying layers are treated (e.g. with retinol) to improve the appearance and suppleness of the skin following the microdermabrasion step.

Retinol is a particularly preferred functional additive in the invented composition because it will help smooth out the treated skin following an abrasive microdermabrasion treatment; i.e. retinol helps counter the negative effects of microdermabrasion such as raw and irritated skin.

The invented microdermabrasion composition has been shown to induce positive alterations in epidermal barrier function. Specifically, skin treated with the invented composition has been found to exhibit improved hydration and reduced transepidermal water loss 7 days following microdermabrasion with the invented composition.

Although the hereinabove described embodiments of the invention constitute the preferred embodiments, it should be understood that modifications can be made thereto without departing from the scope of the invention as set forth in the appended claims.

What is claimed is:

1. An anhydrous microdermabrasion composition comprising at least one water soluble abrasive salt component in an anhydrous fluid medium, said abrasive component being present in said composition in a concentration of 1-25 weight percent, said anhydrous fluid medium comprising:
    (i) a volatile silicone oil in a concentration of 5-25 weight percent;
    (ii) an anhydrous organic solvent, said anhydrous solvent being effective to solvate natural skin oil;
    (iii) a total water soluble emollient concentration of 1-20 weight percent, said water soluble emollient being effective to enhance moisturization properties of said composition on contact thereof with rinsing water;
    (iv) a surfactant in a concentration of 2-60 weight percent; and
    (v) an emollient ester in a concentration of 1-20 weight percent.

2. A composition according to claim 1, said water soluble abrasive component comprising a water soluble salt.

3. A composition according to claim 1, said surfactant being a mixture comprising sodium lauryl sulfoacetate, cetearyl alcohol and ceteareth-20, wherein said sodium lauryl sulfoacetate has a concentration of less than 10 weight percent and said cetearyl alcohol and said ceteareth-20 have a combined concentration of less than 10 weight percent.

4. A composition according to claim 2, said water soluble salt being sodium chloride crystals.

5. A composition according to claim 1, said surfactant being a mixture comprising sodium lauryl sulfoacetate, cetearyl alcohol and ceteareth-20, wherein said sodium lauryl sulfoacetate functions as a mild detergent for cleansing and said cetearyl alcohol and said ceteareth-20 function together as an effective emulsifier to emulsify said composition on contact thereof with water.

6. A composition according to claim 1, further comprising 2-15 weight percent sodium bicarbonate.

7. A composition according to claim 1, wherein said volatile silicone oil is dimethylcyclosiloxane.

8. A composition according to claim 1, said emollient ester being effective to replenish oil removed by said anhydrous solvent.

9. A composition according to claim 1, wherein said emollient ester is caprylic triglyceride, capric triglyceride or a mixture thereof.

10. A composition according to claim 1, further comprising a thickener in a concentration of less than 0.5 weight percent of said composition, said thickener being effective to prevent said silicone oil from separating from said composition.

11. A composition according to claim 10, wherein said thickener is a castor oil based additive.

12. A composition according to claim 1, further comprising vitamin E acetate in a concentration of less than 0.4 weight percent of said composition.

13. A composition according to claim 1, wherein said water soluble emollient comprises silicone glycol copolymer, butylene glycol, or a mixture thereof.

14. A composition according to claim 1, further comprising an antimicrobial agent in a concentration of less than 2 weight percent of said composition.

15. A composition according to claim 1, further comprising a fragrance additive in a concentration of less than 5 weight percent of said composition.

16. A composition according to claim 4, comprising 2-15 weight percent sodium chloride crystals.

17. A composition according to claim 4, comprising 8-25 weight percent sodium chloride crystals.

18. A composition according to claim 4, said sodium chloride crystals having a mean particle size distribution of 50-2000 microns.

19. A composition according to claim 6, said sodium bicarbonate having a mean particle size distribution of 20-500 microns.

20. A composition according to claim 1, said composition being a creamy paste having a viscosity of 500,000-4,000,000 centipoise at 25° C.

21. A composition according to claim 1, further comprising a keratolytic agent in a concentration of less than 4 weight percent of said composition.

22. A composition according to claim 21, said keratolytic agent being selected from the group consisting of salicylic acid, glycolic acid, lactic acid, and mixtures thereof.

23. A composition according to claim 1, further comprising an oxidizing agent in a concentration of less than 18 weight percent of said composition.

24. A composition according to claim 23, said oxidizing agent being benzoyl peroxide.

25. A composition according to claim 1, further comprising an antibacterial component in a concentration of less than 1 weight percent of said composition.

26. A composition according to claim 1, further comprising retinol in a concentration of less than 1 weight percent.

27. A composition according to claim 1, further comprising retinol in a concentration of 0.005-0.5 weight percent.

28. A kit comprising the microdermabrasion composition of claim 1 and an applicator sponge.

29. A kit according to claim 28, said applicator sponge being made from a closed cell polymeric foam.

30. A kit according to claim 28, said applicator sponge having a recess portion effective to retain said composition therein and against a skin surface during a microdermabrasion treatment.

31. A kit according to claim 28, said composition further comprising 8-50 weight percent anhydrous organic solvent, said surfactant, volatile silicone oil and anhydrous organic solvent forming at least a portion of said anhydrous fluid medium.

32. A kit according to claim 28, said applicator sponge comprising flexible polyurethane foam.

33. A kit according to claim 30, said applicator sponge being made from a closed cell polymeric foam.

34. A kit according to claim 28, said applicator sponge further comprising a handle.

35. A method of microdermabrasion comprising the steps of:
  a) providing the microdermabrasion composition of claim 1,;
  b) identifying a target area of one's skin for microdermabrasion treatment;
  c) applying a quantity of said composition to said target area of skin; and
  d) massaging said composition into said target area.

36. A method according to claim 35, wherein said composition is massaged into said target area of skin by a rotary motion for 1-8 revolutions per surface area of skin to be treated.

37. A method according to claim 35, wherein said microdermabrasion composition further comprises at least one functional additive selected from the group consisting of a keratolytic agent, an oxidizer, an antibacterial component, and a skin smoothing agent, said method further comprising the step of:
  e) following said step (d), wetting said composition on said target skin area to activate said at least one functional additive.

38. A method according to claim 37, wherein said wetted composition is left on said target skin area for 10 seconds to 4 minutes.

39. A method according to claim 37, said skin smoothing agent being retinol.

40. A method according to claim 37, said keratolytic agent being salicylic acid.

41. A method according to claim 35, wherein said method is performed bi-weekly or monthly.

42. A microdermabrasion composition according to claim 1, said water soluble abrasive component comprising a mixture of abrasive components including:
  a first water soluble abrasive component present in a concentration of 1-15 weight percent in said composition and having a mean particle size distribution in the range of 5-2000 microns, and
  a second water soluble abrasive component present in a concentration of 2-15 weight percent in said composi tion and having a mean particle size distribution in the range of 20-500 microns.

43. A composition according to claim 42, said first water soluble abrasive component having a mean particle size distribution in the range of 150-850 microns, and said second water soluble abrasive component having a mean particle size distribution in the range of 100-300 microns.

44. A composition according to claim 42, said first and second water soluble abrasive components being sodium chloride and sodium bicarbonate, respectively.

45. A composition according to claim 43, said first and second water soluble abrasive components being sodium chloride and sodium bicarbonate, respectively.

46. A composition according to claim 42, said total water soluble emollient concentration being 1-15 weight percent of said composition and is effective to enhance or provide moisturization properties to said composition on contact thereof with rinsing water.

* * * * *